(12) United States Patent
Pond (10) Patent No.: US 7,048,120 B2
(45) Date of Patent: May 23, 2006

(54) PACKAGE CONSTRUCTION FOR FLUID APPLICATOR DEVICE

(76) Inventor: Gary J. Pond, 2816 N. Main St., Racine, WI (US) 53404

( * ) Notice: Subject to any disclaimer, the term of this patent is extended or adjusted under 35 U.S.C. 154(b) by 93 days.

(21) Appl. No.: 10/449,835

(22) Filed: May 30, 2003

(65) Prior Publication Data

US 2004/0238391 A1 Dec. 2, 2004

(51) Int. Cl.
*A61B 19/02* (2006.01)
*B65D 83/10* (2006.01)

(52) U.S. Cl. ............... 206/366; 206/369; 206/63.5; 206/570

(58) Field of Classification Search ............ 206/369, 206/570, 571, 63.5, 438, 370; 433/226, 215, 433/77
See application file for complete search history.

(56) References Cited

U.S. PATENT DOCUMENTS

| | | | |
|---|---|---|---|
| 1,711,516 A | | 5/1929 | Aland |
| 2,145,570 A | | 3/1939 | Miettunen |
| RE25,483 E | | 11/1963 | Lemos |
| 4,293,074 A | * | 10/1981 | Dunsky ............... 206/572 |
| 4,523,679 A | * | 6/1985 | Paikoff et al. ......... 206/370 |
| 4,863,451 A | * | 9/1989 | Marder ............... 604/403 |
| 4,997,371 A | | 3/1991 | Fischer |
| 5,199,567 A | * | 4/1993 | Discko, Jr. ............ 206/369 |
| 5,286,257 A | | 2/1994 | Fischer |
| 5,289,919 A | * | 3/1994 | Fischer ............... 206/571 |
| 5,816,804 A | | 10/1998 | Fischer |
| 6,079,979 A | | 6/2000 | Riitano |
| 6,162,202 A | | 12/2000 | Sicurelli et al. |
| 6,202,897 B1 | * | 3/2001 | Martin et al. .......... 222/386 |
| D441,074 S | | 4/2001 | Mark |
| 6,238,120 B1 | | 5/2001 | Mark |
| D444,229 S | | 6/2001 | Mark |
| D447,242 S | | 8/2001 | Mark |
| 6,343,929 B1 | | 2/2002 | Fischer |
| 6,382,972 B1 | | 5/2002 | Fischer et al. |
| 6,390,817 B1 | | 5/2002 | Jensen |
| 6,450,810 B1 | | 9/2002 | Fischer et al. |
| 2002/0090691 A1 | | 7/2002 | Fischer |
| 2002/0172921 A1 | | 11/2002 | Jensen |
| 2004/0004019 A1 | * | 1/2004 | Busch ............... 206/571 |
| 2004/0091839 A1 | * | 5/2004 | Fischer ............... 433/226 |

* cited by examiner

*Primary Examiner*—David T. Fidei
(74) *Attorney, Agent, or Firm*—Ryan Kromholz & Manion, S.C.

(57) ABSTRACT

A package construction for a device for applying dental fluids including a plurality of syringes, each syringe having a fluid chamber and an outlet, said chamber containing a fluid selected from the group consisting of carries detection, sodium hypochlorite and hemostatic agent; a plurality of disposable tips, each tip adapted to be attached to one of said syringes at said outlet; and a molded plastic tray, said tray having a plurality of receptacles formed therein for receiving and retaining said syringes and at least one receptacle formed therein for receiving said tips. A removable cover is also provided.

14 Claims, 6 Drawing Sheets

PACKAGE CONSTRUCTION FOR FLUID APPLICATOR DEVICE

BACKGROUND OF THE INVENTION

The present invention relates to an apparatus for applying selected fluids to the teeth or oral cavity of a dental patient directly from a delivery device. Specifically, the present invention relates to a novel combination of a delivery device, disposable tip, pre-selected fluid and storage means.

There exists a need for a fluid applicator device that can be used to apply pre-selected dental fluids to a patient. Heretofore, no one has supplied the components of the present invention in a single source kit form.

In performing various dental procedures, dentists routinely apply selected fluids to the teeth, gums or oral cavity of the mouth of a patient. The fluids can be purchased or acquired in a variety of ways. They can be purchased in bulk containers whereby the dentist or other dental professional must then transfer the fluid into smaller containers for delivery to an individual patient. The fluids can be purchased in small foil packets. Again, the contents of each packet must be transferred to the selected delivery apparatus. However, whenever fluid is transferred, there always exits the risks of contaminating the fluid, spilling the fluid or increasing waste associated with the need for additional containers. The fluids can be purchased in sealed applicator tips. This system has the advantage in that it is not necessary to transfer the fluid from one container to the next prior to use. It should be noted that because of the small volume within such tips, purchasing the fluids in sealed applicator tips tends to add substantially to the fluid's cost.

In the case of fluid supplied in bulk, there are numerous ways of applying the fluid to the dental site. One way is to simply transfer the fluid into a smaller container and then use a brush to apply the fluid to the designated area. The brush may have bristles, much like a common paint brush or have small fibers adhered to its working end.

A second method of application includes transferring the fluid into a reusable syringe. While eliminating the need for a smaller container and separate brush, the syringe must be cleaned after each use. The possibility of spilling and/or contaminating the fluid also still exists.

In a third common way of distributing dental fluids, a single dose is prepackaged in a foil-like container. The container can be opened by simply tearing away a portion of the foil and then a brush or other applicator can be dipped into the open pouch. As in the above described distribution methods, the possibility of spillage and contamination still exist.

While many fluids are utilized by dentists for purposes of supplying dental treatment, the present invention is directed towards carries detection fluids, sodium hypochlorite and hemostatic agents.

SUMMARY OF THE INVENTION

The invention is best described as a package construction for a device for applying dental fluids including a plurality of syringes, each syringe having a fluid chamber and an outlet, said chamber containing a fluid selected from the group consisting of carries detection, sodium hypochlorite and hemostatic agent; a plurality of disposable tips, each tip adapted to be attached to one of said syringes at said outlet; and a molded plastic tray, said tray having a plurality of receptacles formed therein for receiving and retaining said syringes and at least one receptacle formed therein for receiving said tips. In a preferred embodiment the package construction further includes a cover that can be removably attached to the tray. The tips have a variety of tip end configurations including straight tips, bent tips, flocked tips and bristle or brush tips. In another preferred embodiment, all of the package components including the syringes, tips and tray are disposable.

An alternate embodiment may be described as a package construction for a plurality of syringes each containing a pre-selected fluid therein, the package construction including a plurality of syringes, each syringe having a fluid chamber and an outlet, said chamber containing a fluid selected from the group consisting of carries detection, sodium hypochlorite and hemostatic agent; a plurality of disposable tips, each tip adapted to be attached to one of said syringes at said outlet; and a molded plastic tray, said tray having a plurality of receptacles formed therein for receiving and retaining said syringes and at least one receptacle formed therein for receiving said tips.

In yet another embodiment, the invention may be described as a package construction for a plurality of tips having pre-selected end configurations, the package construction including a plurality of syringes, each syringe having a fluid chamber and an outlet, said chamber containing a fluid selected from the group consisting of carries detection, sodium hypochlorite and hemostatic agent; a plurality of disposable tips selected from the group consisting of straight tips, bent tips, brush tips and flocked tips, each tip adapted to be attached to one of said syringes at said outlet; and a molded plastic tray, said tray having receptacles formed therein for receiving and retaining said syringes and at least one receptacle formed therein for receiving said tips.

DESCRIPTION OF THE PREFERRED EMBODIMENT

Figure 1:
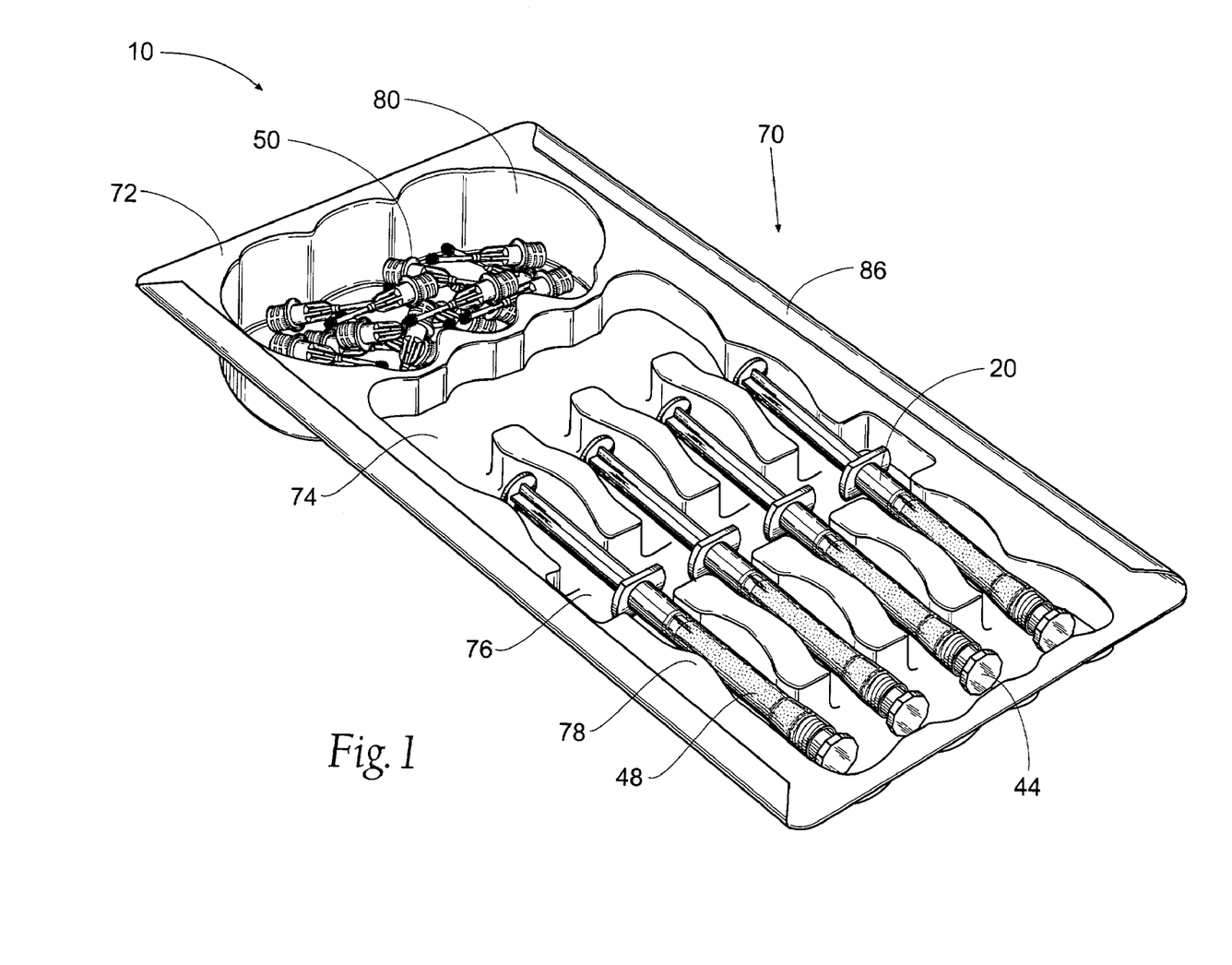
FIG. 1 is a perspective view of the present invention with the cover removed.
Figure 8:
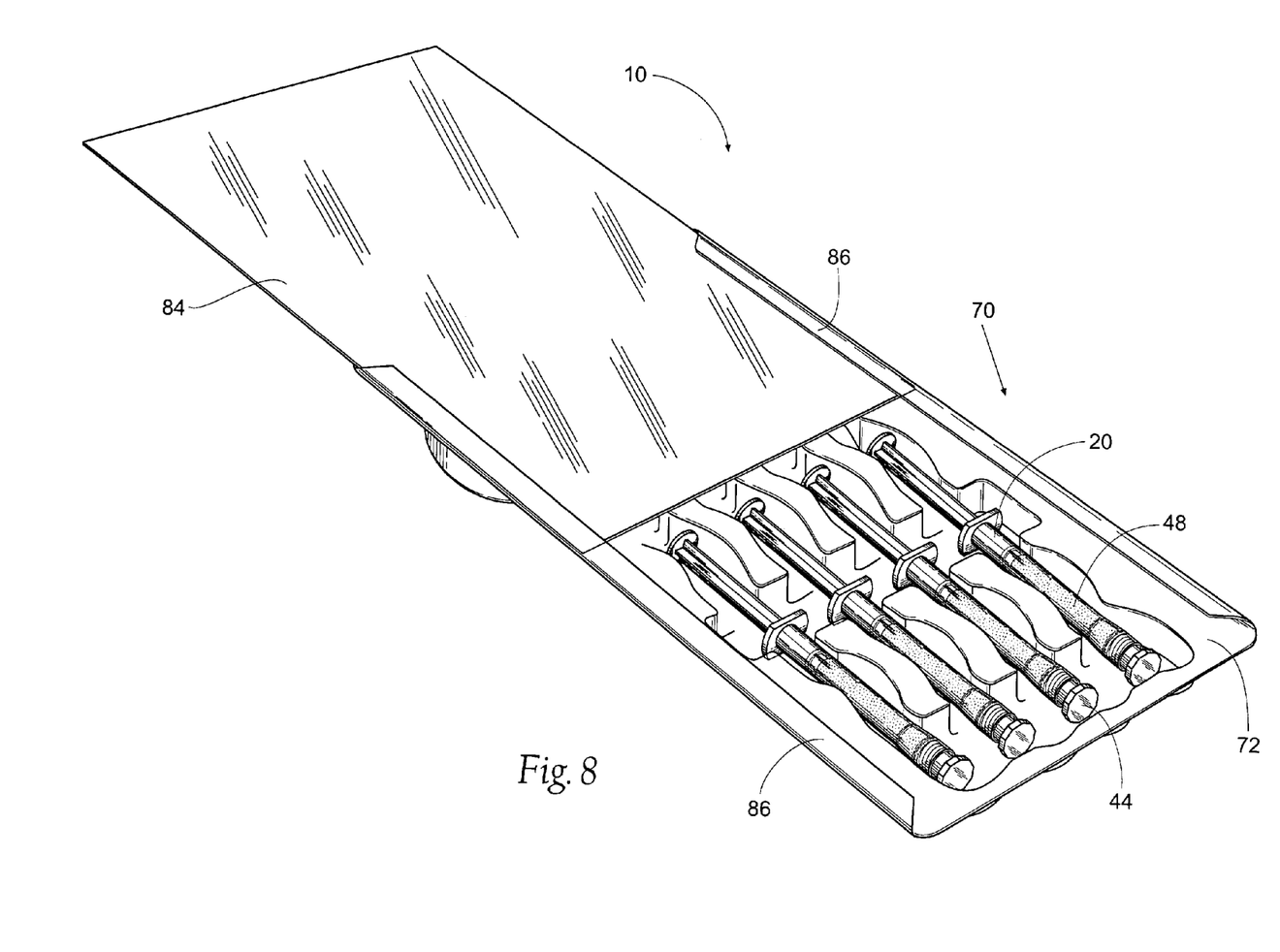
FIG. 8 is a perspective view of the present invention with the cover partially attached.

The following is a description of the preferred embodiment of the invention in which like reference numerals represent like parts throughout the views. The present invention, designated by the reference numeral 10 comprises a kit for use in a dental operatory and is best shown in FIGS. 1 and 8. Referring specifically to FIG. 1, the kit 10 includes one or more syringes 20, each filled with a pre-selected fluid 48, one or more removable tips 50 and storage packaging 70 for the syringe(s) 20 and tip(s) 50. The syringe 20 and tip 50 components are preferably disposable. Each syringe 20 is pre-filled with either a carries detection fluid, sodium hypochlorite or a hemostatic agent 48.

Figure 2:
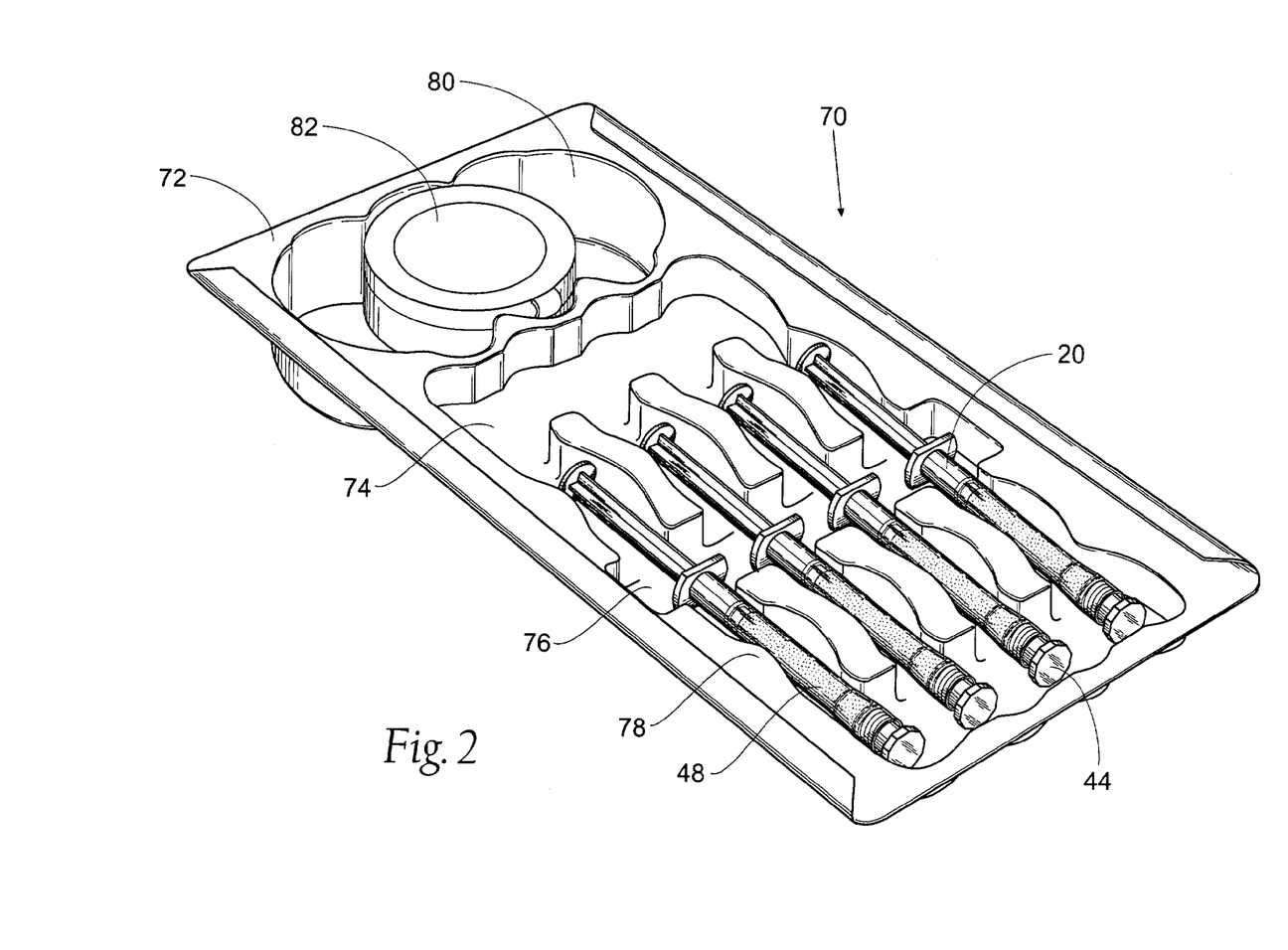
FIG. 2 is a perspective view of the present invention showing a separate single container for the tips.
Figure 3:
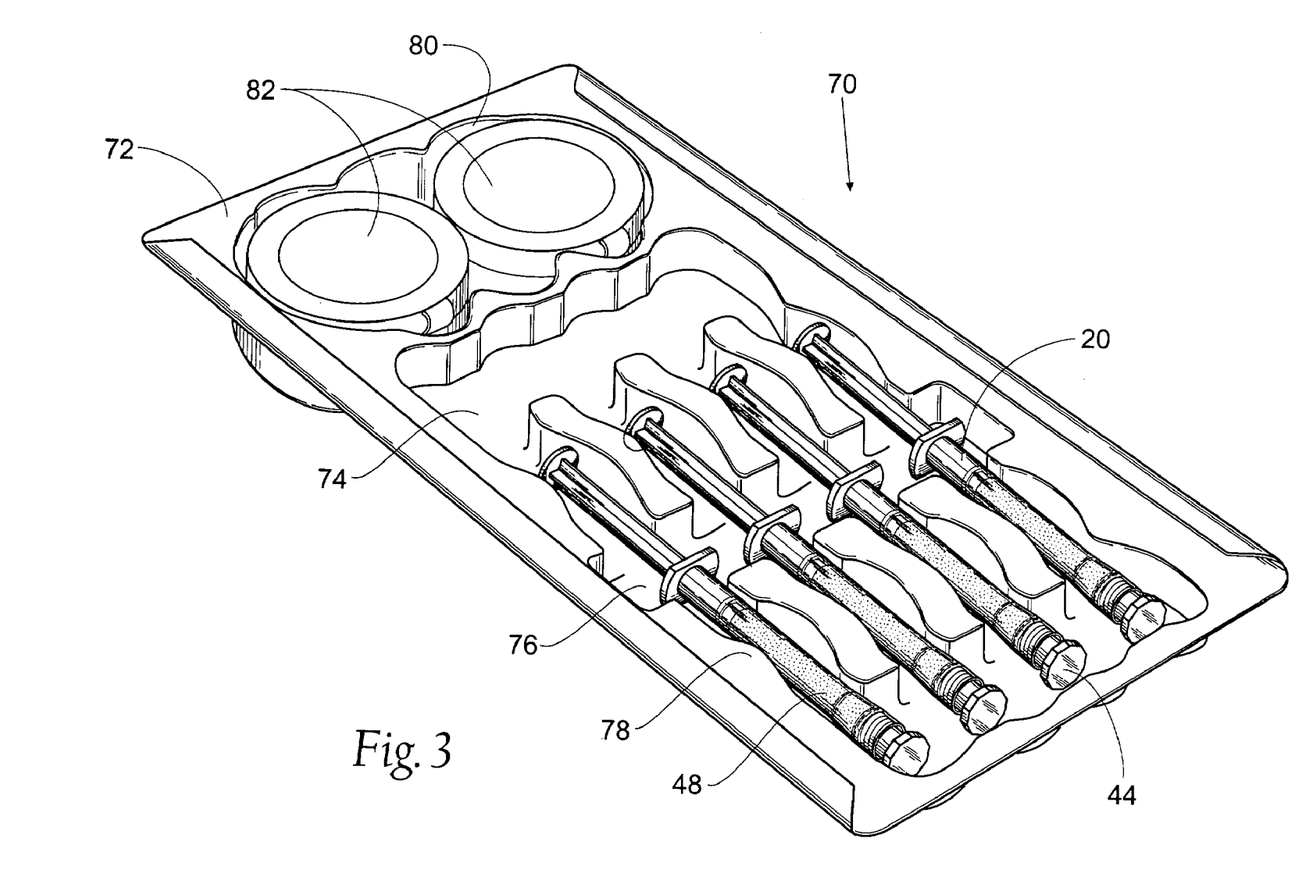
FIG. 3 is a perspective view of the present invention showing two containers for the tips.
Figure 4:
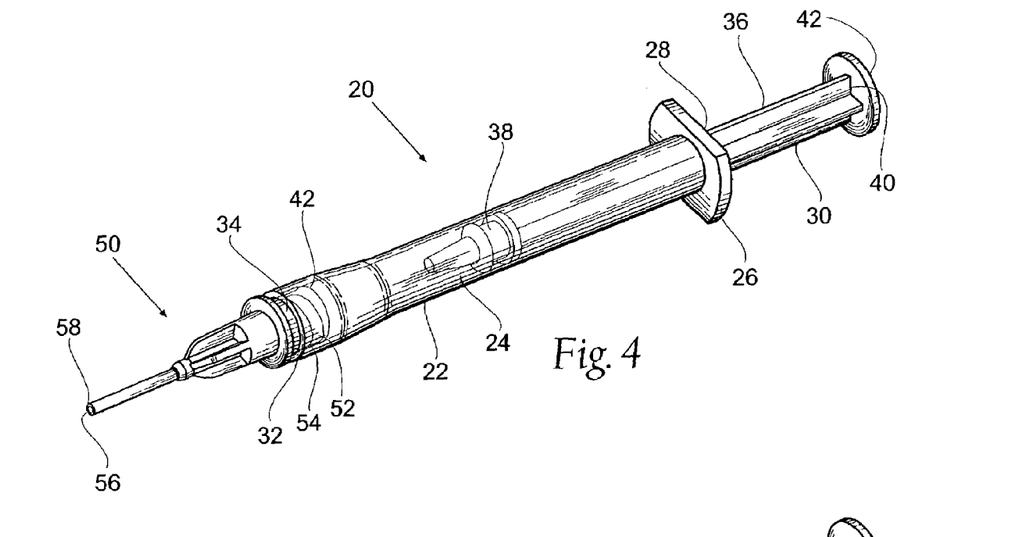
FIG. 4 is a perspective view of an assembled fluid delivery system.

As shown in FIGS. 4 through 7, each syringe includes a main body 22 defining an interior cavity 24 and an upper griping surface 26. The interior cavity includes two openings. A first opening 28 receives the plunger assembly 30 and the second opening 32 comprises the fluid outlet 34. The selected fluid 48 (see FIGS. 1 through 3) occupies the cavity 24. The plunger assembly 30 is positioned within the first opening 28 and includes an elongated member 36 having a first end 38 that sealingly engages with the interior cavity 24 and a second end 40 including a thumb pad 42 for application of pressure to the syringe 20.

Figure 5:
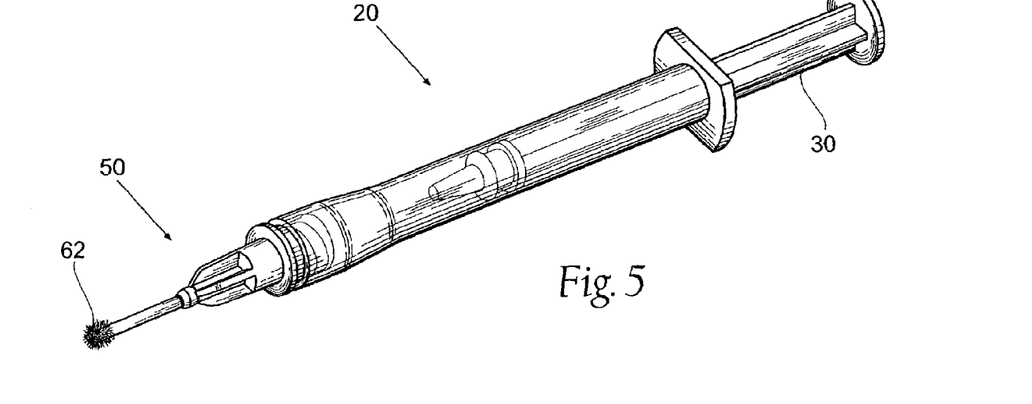
FIG. 5 is a perspective view of an alternate assembled fluid delivery system.
Figure 6:
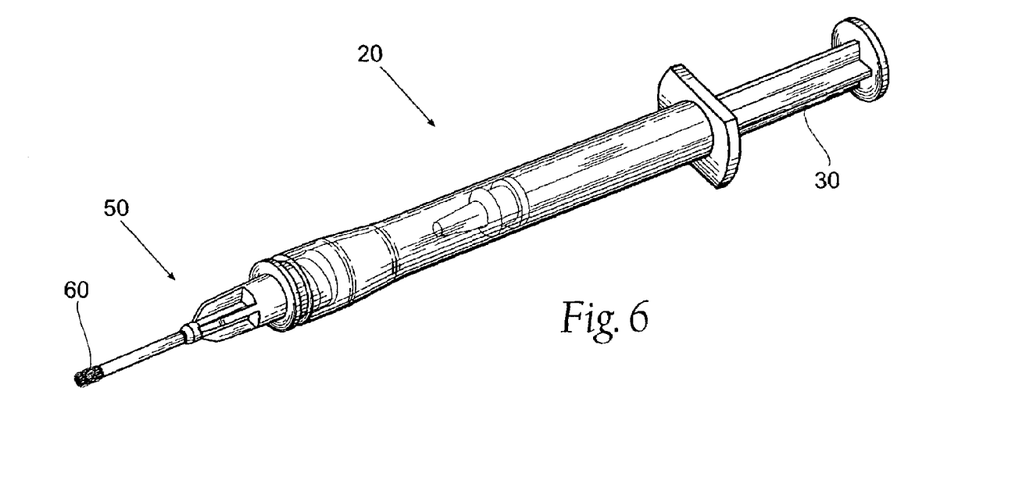
FIG. 6 is another perspective view of another alternate assembled fluid delivery system.
Figure 7:
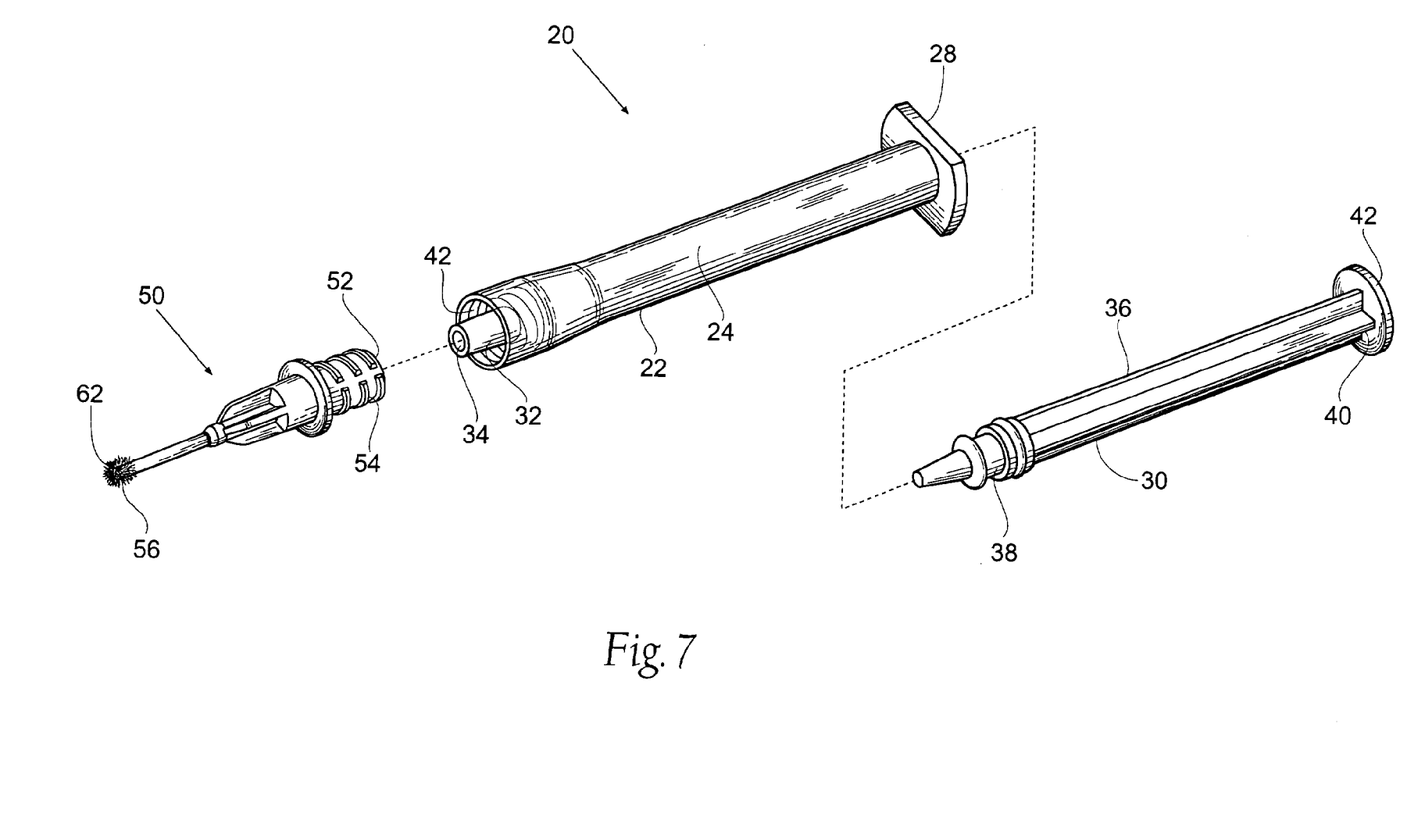
FIG. 7 is an exploded view of a fluid delivery system.

The outlet 34 includes a separable connection mechanism 42 for receiving and attaching a disposable tip 50. In a preferred embodiment, a LUER® style locking configuration is used. As best shown in FIG. 7, the disposable tips 50 include an inlet end 52 and an outlet end 56. The inlet end 52 includes a separable connection mechanism 54 that mates with connection 42. The inlet end 52 couples to the syringe outlet 34 with, for example, the LUER® style locking configuration. The outlet end 56 may simply include an aperture 58 (see FIG. 4) for the fluid 48 to flow through or may include additional structure such as brush bristles 60 or fibers 62 as shown in FIGS. 6 and 5, respectively. The bristles 60 and fibers 62 can be of any pre-selected length and/or diameter and are adhered to the outlet end 56 of the tip 50 using conventional techniques. A tip 50 having a plurality of fibers 62 attached thereto is commonly known as a flocked applicator or flocked tip. A tip 50 having a plurality of bristles attached thereto is commonly known as a brush applicator or brush tip.

As shown in FIGS. 1 through 3 and 8, the package construction 70 includes a tray 72 having a number of cavities 74 for receiving and holding the syringes 20 and tips 50. Each of the plurality of syringes 20 is retained in a separate elongate cavity 76. Each syringe cavity 76 includes a gripping structure 78 for frictionally retaining each syringe. A larger cavity 80 is provided for the tips 50. In a preferred embodiment, an oval shaped cavity is provided for the tips. The tips 50 may be placed directly in the cavity 80 or the tips may be placed in a separate container 82 that is sized to be received within the larger cavity 80. In a preferred embodiment, the oval shaped cavity is dimensioned to receive two tip containers 82 spaced apart in a side-by-side relationship. A removable cover 84, secured by cover retention members 86 may be placed over the tray 72 before use or in between uses.

Each syringe 20 is pre-filled with one of three pre-selected fluids 48. Once filled, a plug 44 is attached to the syringe outlet 34 to seal the fluid within the interior cavity 24 and prevent contamination of the fluid 48. The first fluid is carries detection fluid, also called dentine carries dye. Carries detection fluid is useful for identification of fissure carries, inner carious dentine in clinically accessible lesions and occlusal carious lesions. The fluid stains the denatured collagen in the inner part of the lesion thereby allowing the dentist to positively identify the lesion. Once the fluid is applied, the excess is rinsed away and the area is examined for residual staining which is an indication of the presence of dentine caries.

The second fluid is sodium hypochlorite. Sodium hypochlorite fluid is utilized in root canal treatment for its antimicrobial properties. In addition, sodium hypochlorite is known to denature toxins and dissolve organic tissue. Once the dentine has been exposed and the diseased tissue mechanically removed from the canal, a solution of sodium hypochlorite in the range of 0.5 to 7% is used to clean and flush the canal.

The third fluid includes hemostatic agents. Hemostatic agents are used primarily to control bleeding in the gingival surfaces of the mouth, namely the gums. Often during a dental procedure, the gingival surface must be cut or disrupted. A hemostatic agent such as VISCOSTAT®, ASTRINGEDENT® manufactured by Ultradent Products of South Jordan, Utah, and HEMODENT® manufactured by Stone Pharmaceuticals of Philadelphia, Pa. is applied to the affected area to substantially stop the bleeding.

In use, the dentist removes a syringe 20 containing the pre-selected fluid 48 from the storage packaging 70. The plug 44 is removed from the syringe outlet 34 and a tip 50 is connected. If necessary during the dental procedure, a first selected tip 50 can be removed and a different tip 50 can be replaced on the syringe 20. When the procedure is complete, the syringe 20, any remaining fluid 48, and any used tips 50 are preferably disposed. The remaining, unused components can be utilized in subsequent dental procedures.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A package construction comprising a prepackaged set of components for a device for applying dental fluids, said package construction comprising:

a plurality of syringes, each syringe having a fluid chamber and an outlet, said chamber containing a fluid selected from the group consisting of carries detection, sodium hypochlorite and hemostatic agent, said syringed being prefilled with said fluid prior to being packaged, each of syringes including a plug, said plug being removably installed in each of said outlets;

a plurality of disposable tips, each tip adapted to be attached to one of said syringes at said outlet;

a molded plastic tray, said tray having a plurality of syringe receptacles formed therein for receiving and retaining said syringes, each of said syringe receptacles being adapted to hold one syringe, and at least one tip receptacle formed therein for receiving said tips.

2. The package construction of claim 1 further including a cover, the cover being removably attached to the tray.

3. The package construction of claim 1 wherein each tip has a flocked applicator end.

4. The package construction of claim 1 wherein each tip has a brush applicator end.

5. The package construction of claim 1 wherein each tip is selected from the group consisting of straight tips, bent tips, brush tips and flocked tips.

6. The package construction of claim 1 wherein the syringes, tips and tray are all disposable.

7. A package construction comprising a prepackaged plurality of syringes each containing a pre-selected fluid therein, said pre-selected fluids specially selected for the detection and treatment of dental lesions, the package construction comprising:

a plurality of syringes, each syringe having a fluid chamber and an outlet, said chamber containing a fluid selected from the group consisting of carries detection, sodium hypochlorite and hemostatic agent each of said syringes including a plug, said plug being removably installed in each of said outlets;

a plurality of disposable tips, each tip adapted to be attached to one of said syringes at said outlet;

a molded plastic tray, said tray having a plurality of syringe receptacles formed therein for receiving and retaining said syringes, each of said syringe receptacles being adapted to hold one syringe, and at least one tip receptacle formed therein for receiving said tips.

8. The package construction of claim 1 further including a cover, the cover being removably attached to the tray.

9. The package construction of claim 7 wherein each tip has a flocked applicator end.

10. The package construction of claim 7 wherein each tip has a brush applicator end.

11. The package construction of claim 7 wherein each tip is selected from the group consisting of straight tips, bent tips, brush tips and flocked tips.

12. The package construction of claim 7 wherein the syringes, tips and tray are all disposable.

13. A package construction comprising a plurality of prepackaged syringes and a plurality of tips having preselected end configurations and specially selected for the detection of dental lesions and the treatment of the dental lesions, the package construction comprising:

a plurality of syringes, each syringe having a fluid chamber and an outlet, said chamber containing a fluid selected from the group consisting of carries detection, sodium hypochlorite and hemostatic agent, said syringes being prefilled with said solution prior to being packaged, each of said syringes further including a plug said plug being removably installed in each of said outlets;

a plurality of disposable tips selected from the group consisting of straight tips, bent tips, brush tips and flocked tips, each tip adapted to be attached to one of said syringes at said outlet;

a molded plastic tray, said tray having syringe receptacles formed therein for receiving and retaining said syringes, each of said syringe receptacles being adapted to hold one syringe, and at least one tip receptacle formed therein for receiving said tips; and a cover, the cover being removably attached to the tray.

14. The package construction of claim 13 wherein the syringes, tips and tray are all disposable.

* * * * *

UNITED STATES PATENT AND TRADEMARK OFFICE
CERTIFICATE OF CORRECTION

PATENT NO. : 7,048,120 B2  Page 1 of 1
APPLICATION NO. : 10/449835
DATED : May 23, 2006
INVENTOR(S) : Gary J. Pond

It is certified that error appears in the above-identified patent and that said Letters Patent is hereby corrected as shown below:

On Title Page, Item (56) under U.S. Patent Documents, delete "2002/0090691" and insert -- 2002/0090591 --

Column 6, line 7, after "a plug" insert -- , -- (comma)

Signed and Sealed this

Third Day of April, 2007

JON W. DUDAS
*Director of the United States Patent and Trademark Office*